United States Patent
Deyev et al.

(10) Patent No.: US 8,383,575 B2
(45) Date of Patent: Feb. 26, 2013

(54) (DI)BARNASE-BARSTAR COMPLEXES

(75) Inventors: Sergey Deyev, Moscow (RU); Robert Waibel, Raeterschen (CH); Andreas Plueckthun, Zurich (CH)

(73) Assignee: Paul Scherrer Institut, Villigen (CH)

( * ) Notice: Subject to any disclaimer, the term of this patent is extended or adjusted under 35 U.S.C. 154(b) by 403 days.

(21) Appl. No.: 11/045,502

(22) Filed: Jan. 31, 2005

(65) Prior Publication Data

US 2006/0120960 A1 Jun. 8, 2006

Related U.S. Application Data

(60) Provisional application No. 60/539,976, filed on Jan. 30, 2004.

(51) Int. Cl.
*A61K 8/64* (2006.01)
*C07K 14/00* (2006.01)
*C07K 14/195* (2006.01)

(52) U.S. Cl. ....... 514/1.1; 514/21.2; 514/21.3; 530/300; 530/350; 424/1.69

(58) Field of Classification Search .................... None
See application file for complete search history.

(56) References Cited

U.S. PATENT DOCUMENTS 5,328,984 A * 7/1994 Pastan et al. ............... 424/134.1

FOREIGN PATENT DOCUMENTS

WO   WO 92/09696 A   6/1992

OTHER PUBLICATIONS

Hartley Robert W., Barnase and Barstar Expression of Its Cloned Inhibitor Permits Expression of a Cloned Ribonuclease, Journal of Molecular Biology, 1988, 202: 913-915.*
Deyev SM, Waibel R, Lebedenko EN, Schubiger AP, Pluckthun A, Design of multivalent complexes using the barnase*barnase module, Nature Biotechnology, Nov. 2003, 21(12): 1486-1492.*
Definition of derivative from http://cancerweb.ncl.ac.uk/omd/about. html, pp. 1-5. Accessed Jul. 7, 2005.*
Hartley et al. "Directed mutagenesis and barnase-barstar recognition." *Biochemistry* 32:5978-5984, 1993.
Pathare et al. "Synthesis of cobalamin-biotin conjugates that vary in the position of cobalamin coupling. Evaluation of cobalamin derivative binding to transcobalamin II." *Bioconjug Chem*. Mar.-Apr. 1996;7(2):217-32 (Abstract).
Martsev et al. "Fusion of the antiferritin antibody VL domain to barnase results in enhanced solubility and altered pH stability." *Protein Engineering, Design & Selection* vol. 17 No. 1 pp. 85-93, 2004.

* cited by examiner

*Primary Examiner* — Julie Ha
(74) *Attorney, Agent, or Firm* — Laurence A. Greenberg; Werner H. Stemer; Ralph E. Locher

(57) ABSTRACT

A complex comprising barnase bound with high affinity to barstar, and comprising a therapeutic and/or diagnostic agent bound to barnase and/or barstar.

8 Claims, 4 Drawing Sheets

SEQUENCE LISTING

<160> NUMBER OF SEQ ID NOS: 61

<210> SEQ ID NO 1
<211> LENGTH: 31
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 1
tggcgcgccg aaaaaagcag tcattaacgg g                           31

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggcgcgcca gaaagtatga tggtgatgtc                             30

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtggcgcgcc tgcacaggtt atcaacacgt ttg                         33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtgcggcgcg cctctgattt ttgtaaaggt ctg                         33

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgtctaagct tgatgaaaaa agcagtcatt aacg                        34

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aacagctatg accatgatta cg                                     22

<210> SEQ ID NO 7
<211> LENGTH: 27
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 7
atcagacctt tacaaaaagc ttataac                                               27

<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagaccttta caaaaatcag agacacgttt gacggggttg c                               41

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gcaaccccgt caaacgtgtc tctgattttt gtaaaggtct g                               41

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5

<210> SEQ ID NO 11
<211> LENGTH: 110
<212> TYPE: PRT
<213> ORGANISM: Bacillus amyloliquefaciens

<400> SEQUENCE: 11

Ala Gln Val Ile Asn Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
                20                  25                  30

Leu Gly Trp Val Ala Ser Lys Gly Asn Leu Ala Asp Val Ala Pro Gly
            35                  40                  45

Lys Ser Ile Gly Gly Asp Ile Phe Ser Asn Arg Glu Gly Lys Leu Pro
        50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
                100                 105                 110

<210> SEQ ID NO 12
<211> LENGTH: 89
<212> TYPE: PRT
```

<213> ORGANISM: Bacillus amyloliquefaciens

<400> SEQUENCE: 12

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
        35                  40                  45

Leu Val Leu Glu Trp Arg Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 13
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Ala Leu Thr Gly Trp Val Glu Tyr Pro
        35                  40                  45

Leu Val Leu Glu Trp Arg Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Ala Asp Ile Thr Ile Ile Leu Ser
                85

<210> SEQ ID NO 14
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Lys Ala Val Ile Asn Gly Glu Gln Ile Arg Ser Ile Ser Asp Leu
1               5                   10                  15

His Gln Thr Leu Asn Asn Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
        35                  40                  45

Leu Val Leu Glu Trp Arg Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

```
<210> SEQ ID NO 15
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Lys Ala Leu Trp Asp Cys Leu Thr Gly Trp Val Glu Tyr Pro
        35                  40                  45

Leu Val Leu Glu Trp Arg Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 16
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Lys Cys Leu Thr Gly Trp Val Glu Tyr Pro
        35                  40                  45

Leu Val Leu Glu Trp Arg Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 17
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Asn Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
        35                  40                  45

Leu Val Leu Glu Trp Arg Gln Phe Glu Gln Ser Lys Gln Leu Thr Glu
    50                  55                  60
```

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 18
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Lys Ala Val Ile Asn Gly Lys Gln Ile Arg Ser Ile Ser Asp Leu
1               5                   10                  15

His Gln Thr Leu Lys Lys Glu Leu Ala Leu Pro Glu Tyr Tyr Gly Glu
                20                  25                  30

Asn Leu Asp Ala Leu Trp Asp Cys Leu Thr Gly Trp Val Glu Tyr Pro
            35                  40                  45

Leu Val Leu Glu Trp Arg Gln Phe Glu Gln Ser Lys Gln Leu Thr Glu
        50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 19
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Lys Ala Val Ile Asn Gly Glu Gln Ile Arg Ser Ile Ser Lys Leu
1               5                   10                  15

His Gln Thr Leu Lys Lys Glu Leu Ala Leu Pro Glu Tyr Tyr Gly Glu
                20                  25                  30

Asn Leu Asp Ala Leu Trp Asp Cys Leu Thr Gly Trp Val Glu Tyr Pro
            35                  40                  45

Leu Val Leu Glu Trp Arg Gln Phe Glu Gln Ser Lys Gln Leu Thr Glu
        50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 20
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Lys Ala Val Ile Asn Gly Glu Gln Ile Arg Ser Ile Ser Asp Leu
1               5                   10                  15

His Gln Thr Leu Gln Lys Glu Leu Ala Leu Pro Glu Tyr Tyr Gly Glu

```
                    20                  25                  30
Asn Leu Asp Ala Leu Trp Asp Cys Leu Thr Gly Trp Val Glu Tyr Pro
            35                  40                  45

Leu Val Leu Glu Trp Arg Gln Phe Glu Gln Ser Lys Gln Leu Thr Glu
        50                  55                  60

Asn Gly Ala Glu Ser Val Leu Gln Val Phe Arg Glu Ala Lys Ala Glu
 65                  70                  75                  80

Gly Cys Asp Ile Thr Ile Ile Leu Ser
                85

<210> SEQ ID NO 21
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Lys Ala Val Ile Asn Gly Glu Gln Ile Arg Ser Ile Ser Asp Leu
 1               5                  10                  15

His Gln Thr Leu Lys Glu Lys Leu Ala Leu Pro Glu Tyr Tyr Gly Glu
            20                  25                  30

Asn Leu Asp Ala Leu Trp Asp Cys Leu Thr Gly Trp Val Glu Tyr Pro
            35                  40                  45

Leu Val Leu Glu Trp Arg Gln Phe Glu Gln Ser Lys Gln Leu Thr Glu
        50                  55                  60

Asn Gly Ala Glu Ser Val Leu Gln Val Phe Arg Glu Ala Lys Ala Glu
 65                  70                  75                  80

Gly Cys Asp Ile Thr Ile Ile Leu Ser
                85

<210> SEQ ID NO 22
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Lys Ala Val Ile Asn Gly Glu Gln Ile Arg Ser Ile Ser Asp Leu
 1               5                  10                  15

His Gln Thr Leu Lys Lys Glu Leu Ala Leu Pro Lys Tyr Tyr Gly Glu
            20                  25                  30

Asn Leu Asp Ala Leu Trp Asp Cys Leu Thr Gly Trp Val Glu Tyr Pro
            35                  40                  45

Leu Val Leu Glu Trp Arg Gln Phe Glu Gln Ser Lys Gln Leu Thr Glu
        50                  55                  60

Asn Gly Ala Glu Ser Val Leu Gln Val Phe Arg Glu Ala Lys Ala Glu
 65                  70                  75                  80

Gly Cys Asp Ile Thr Ile Ile Leu Ser
                85

<210> SEQ ID NO 23
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 23

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Lys
            20                  25                  30

Asn Leu Asp Ala Leu Trp Asp Cys Leu Thr Gly Trp Val Glu Tyr Pro
        35                  40                  45

Leu Val Leu Glu Trp Arg Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 24
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Lys Tyr Pro
        35                  40                  45

Leu Val Leu Glu Trp Arg Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 25
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
        35                  40                  45

Leu Val Leu Lys Trp Arg Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

```
<210> SEQ ID NO 26
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
        35                  40                  45

Leu Val Leu Glu Trp Ser Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 27
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
        35                  40                  45

Leu Val Leu Glu Trp Arg Gln Phe Lys Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 28
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
        35                  40                  45

Leu Val Leu Glu Trp Arg Gln Phe Glu Gln Ser Glu Gln Leu Thr Glu
    50                  55                  60
```

Asn Gly Ala Glu Ser Val Leu Gln Val Phe Arg Ala Lys Ala Glu
65                  70                  75                  80

Gly Cys Asp Ile Thr Ile Ile Leu Ser
                85

<210> SEQ ID NO 29
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
        35                  40                  45

Leu Val Leu Glu Trp Arg Gln Phe Glu Gln Ser Lys Gln Leu Thr Lys
    50                  55                  60

Asn Gly Ala Glu Ser Val Leu Gln Val Phe Arg Glu Ala Lys Ala Glu
65                  70                  75                  80

Gly Cys Asp Ile Thr Ile Ile Leu Ser
                85

<210> SEQ ID NO 30
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
        35                  40                  45

Leu Val Leu Glu Trp Arg Gln Phe Glu Gln Ser Lys Gln Leu Thr Glu
    50                  55                  60

Asn Gly Ala Lys Ser Val Leu Gln Val Phe Arg Glu Ala Lys Ala Glu
65                  70                  75                  80

Gly Cys Asp Ile Thr Ile Ile Leu Ser
                85

<210> SEQ ID NO 31
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
                35                  40                  45

Leu Val Leu Glu Trp Arg Gln Phe Glu Gln Ser Lys Gln Leu Thr Glu
         50                  55                  60

Asn Gly Ala Glu Ser Val Leu Gln Val Phe Glu Arg Ala Lys Ala Glu
65                  70                  75                  80

Gly Cys Asp Ile Thr Ile Ile Leu Ser
                85

<210> SEQ ID NO 32
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
                35                  40                  45

Leu Val Leu Glu Trp Arg Gln Phe Glu Gln Ser Lys Gln Leu Thr Glu
         50                  55                  60

Asn Gly Ala Glu Ser Val Leu Gln Val Phe Arg Glu Ala Glu Ala Lys
65                  70                  75                  80

Gly Cys Asp Ile Thr Ile Ile Leu Ser
                85

<210> SEQ ID NO 33
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Cys Leu Thr Gly Trp Val Glu Tyr Pro
                35                  40                  45

Leu Val Leu Glu Trp Arg Gln Phe Glu Gln Ser Lys Gln Leu Thr Glu
         50                  55                  60

Asn Gly Ala Glu Ser Val Leu Gln Val Phe Arg Glu Ala Lys Ala Glu
65                  70                  75                  80

Gly Cys Lys Ile Thr Ile Ile Leu Ser
                85

<210> SEQ ID NO 34
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Gly Leu Thr Gly Trp Val Glu Tyr Pro
        35                  40                  45

Leu Val Leu Glu Trp Arg Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Gly Asp Ile Thr Ile Ile Leu Ser
                85

<210> SEQ ID NO 35
<211> LENGTH: 89
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Lys Ala Val Ile Asn Gly Glu Gln Ile Arg Ser Ile Ser Asp Leu
1               5                   10                  15

His Gln Thr Leu Lys Lys Glu Leu Ala Leu Pro Glu Tyr Tyr Gly Glu
            20                  25                  30

Asn Leu Asp Ala Leu Trp Asp Ser Leu Thr Gly Trp Val Glu Tyr Pro
        35                  40                  45

Leu Val Leu Glu Trp Arg Gln Phe Glu Gln Ser Lys Gln Leu Thr Glu
    50                  55                  60

Asn Gly Ala Glu Ser Val Leu Gln Val Phe Arg Glu Ala Lys Ala Glu
65                  70                  75                  80

Gly Ser Asp Ile Thr Ile Ile Leu Ser
                85

<210> SEQ ID NO 36
<211> LENGTH: 1287
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: modified_base
<222> LOCATION: (982)..(985)
<223> OTHER INFORMATION: a, c, t, g, unknown or other

<400> SEQUENCE: 36
atctagctaa gtataactgg ataatttgca ttaacagatt gaatatagtg ccaaacaaga      60
agggacaatt gacttgtcac tttatgaaag atgattcaaa catgattttt tatgtactaa    120
tatatacatc ctactcgaat taaagcgaca taggctcgaa gtatgcacat ttagcaatgt    180
aaattaaatc agttttgaa tcaagctaaa agcagacttg cataaggtgg gtggctggac    240
tagaataaac atcttctcta gcacagcttc ataatgtaat tccataact gaaatcaggg    300 tgagacaaaa ttttggtact ttttcctcac actaagtcca tgtttgcaac aaattaatac    360
atgaaacctt aatgttaccc tcagattagc ctgctactcc ccatttcct cgaaatgctc    420 caacaaaagt tagttttgca agttgttgtg tatgtcttgt gctctatata tgcccttgtg    480

```
gtgcaagtgt aacagtacaa catcatcact caaatcaaag ttttttactta aagaaattag    540 ctaccatggt accggttatc aacacgtttg acggggttgc ggattatctt cagacatatc    600
ataagctacc tgataattac attacaaaat cagaagcaca agccctcggc tgggtggcat    660
caaaagggaa ccttgcagac gtcgctccgg ggaaaagcat cggcggagac atcttctcaa    720
acagggaagg caaactcccg ggcaaaagcg gacgaacatg gcgtgaagcg gatattaact    780
atacatcagg cttcagaaat tcagaccgga ttctttactc aagcgactgg ctgatttaca    840
aaacaacgga ccattatcag acctttacaa aaatcagata cgaaaaaaa cggcttcctg    900 cggaggccgt ttttttcagc tttacataaa gtgtgtaata aattttctt caaactctga    960 tcggtcaatt tcactttccg gnnnnctcta gaggatccga agcagatcgt tcaaacattt   1020
ggcaataaag tttcttaaga ttgaatcctg ttgccggtct tgcgatgatt atcatataat   1080
ttctgttgaa ttacgttaag catgtaataa ttaacatgta atgcatgacg ttatttatga   1140
gatgggtttt tatgattaga gtcccgcaat tatacattta atacgcgata gaaaacaaaa   1200
tatagcgcgc aaactaggat aaattatcgc gcgcggtgtc atctatgtta ctagatcggg   1260
aagatccccg ggtaccgagc tcgaatt                                       1287
```

<210> SEQ ID NO 37
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ala Gln Asp Asp Asn Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
                20                  25                  30

Leu Gly Trp Val Ala Ser Lys Gly Asn Leu Ala Asp Val Ala Pro Gly
            35                  40                  45

Lys Ser Ile Gly Gly Asp Ile Phe Ser Asn Arg Glu Gly Lys Leu Pro
        50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
                100                 105                 110

<210> SEQ ID NO 38
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ala Gln Val Asp Ile Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
                20                  25                  30

Leu Gly Trp Val Ala Ser Lys Gly Asn Leu Ala Asp Val Ala Pro Gly
            35                  40                  45

```
Lys Ser Ile Gly Gly Asp Ile Phe Ser Asn Arg Glu Gly Lys Leu Pro
        50                  55                  60

Gly Lys Ser Gly Arg Thr Trp Arg Glu Ala Asp Ile Asn Tyr Thr Ser
 65                  70                  75                  80

Gly Phe Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110

<210> SEQ ID NO 39
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ala Gln Val Ile Asn Thr Phe Lys Gly Val Asp Tyr Leu Gln Thr
 1               5                  10                  15

Tyr Arg Lys Leu Pro Asp Asn Tyr Ile Thr Lys Ser Glu Ala Gln Ala
                 20                  25                  30

Leu Gly Trp Val Ala Ser Lys Gly Asn Leu Ala Asp Val Ala Pro Gly
             35                  40                  45

Lys Ser Ile Gly Gly Asp Ile Phe Ser Asn Arg Glu Gly Lys Leu Pro
        50                  55                  60

Gly Lys Ser Gly Arg Thr Trp Arg Glu Ala Asp Ile Asn Tyr Thr Ser
 65                  70                  75                  80

Gly Phe Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110

<210> SEQ ID NO 40
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ala Gln Val Ile Asn Thr Phe Asp Gly Val Ala Ile Tyr Leu Gln Thr
 1               5                  10                  15

Tyr His Lys Leu Pro Asp Asn Tyr Ile Thr Lys Ser Glu Ala Gln Ala
                 20                  25                  30

Leu Gly Trp Val Ala Ser Lys Gly Asn Leu Ala Asp Val Ala Pro Gly
             35                  40                  45

Lys Ser Ile Gly Gly Asp Ile Phe Ser Asn Arg Glu Gly Lys Leu Pro
        50                  55                  60

Gly Lys Ser Gly Arg Thr Trp Arg Glu Ala Asp Ile Asn Tyr Thr Ser
 65                  70                  75                  80

Gly Phe Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110

<210> SEQ ID NO 41
<211> LENGTH: 110
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 41

Ala Gln Val Ile Asn Thr Phe Asp Gly Val Ala Asp Tyr Leu Gln Thr
1               5                   10                  15

Tyr Arg Lys Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

Lys Ser Ile Gly Gly Asp Ile Phe Ser Asn Arg Glu Gly Lys Leu Pro
    50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 42
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ala Gln Val Ile Asn Thr Phe Asp Gly Val Ala Asp Tyr Leu Gln Thr
1               5                   10                  15

Tyr Arg Glu Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

Lys Ser Ile Gly Gly Asp Ile Phe Ser Asn Arg Glu Gly Lys Leu Pro
    50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 43
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ala Gln Val Ile Asn Thr Phe Asp Gly Val Ala Asp Tyr Leu Gln Thr
1               5                   10                  15

Tyr His Lys Leu Pro Ser Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45
```

```
Lys Ser Ile Gly Gly Asp Ile Phe Ser Asn Arg Glu Gly Lys Leu Pro
            50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 44
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ala Gln Val Ile Asn Thr Phe Asp Gly Val Ala Asp Tyr Leu Gln Thr
1               5                   10                  15

Tyr Arg Lys Leu Pro Asp Asn Tyr Ile Thr Lys Ser Lys Ala Gln Ala
            20                  25                  30

Leu Gly Trp Val Ala Ser Lys Gly Asn Leu Ala Asp Val Ala Pro Gly
        35                  40                  45

Lys Ser Ile Gly Gly Asp Ile Phe Ser Asn Arg Glu Gly Lys Leu Pro
            50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 45
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ala Gln Val Ile Asn Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
            20                  25                  30

Leu Val Trp Gly Ala Ser Lys Gly Asn Leu Ala Asp Val Ala Pro Gly
        35                  40                  45

Lys Ser Ile Gly Gly Asp Ile Phe Ser Asn Arg Glu Gly Lys Leu Pro
            50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 46
<211> LENGTH: 110
<212> TYPE: PRT
```

<213> ORGANISM: Artificial Sequence
<220> FEATURE:
<223> OTHER INFORMATION: Description of Artificial Sequence: Synthetic
    polypeptide

<400> SEQUENCE: 46

Ala Gln Val Ile Asn Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
            20                  25                  30

Leu Gly Trp Val Ala Ser Glu Gly Asn Leu Ala Asp Val Ala Pro Gly
        35                  40                  45

Lys Ser Ile Gly Gly Asp Ile Phe Ser Asn Arg Glu Gly Lys Leu Pro
    50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 47
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 47

Ala Gln Val Ile Asn Thr Phe Asp Gly Val Ala Asp Tyr Leu Gln Thr
1               5                   10                  15

Tyr Arg Lys Leu Pro Asp Asn Tyr Ile Thr Lys Ser Glu Ala Gln Ala
            20                  25                  30

Leu Gly Trp Val Ala Ser Lys Gly Asn Leu Ala Lys Val Ala Pro Gly
        35                  40                  45

Lys Ser Ile Gly Gly Asp Ile Phe Ser Asn Arg Glu Gly Lys Leu Pro
    50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 48
<211> LENGTH: 110
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 48

Ala Gln Val Ile Asn Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

```
Glu Ser Ile Gly Gly Asp Ile Phe Ser Asn Arg Glu Gly Lys Leu Pro
        50                  55                  60

Gly Lys Ser Gly Arg Thr Trp Arg Glu Ala Asp Ile Asn Tyr Thr Ser
 65                  70                  75                  80

Gly Phe Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110

<210> SEQ ID NO 49
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ala Gln Val Ile Asn Thr Phe Asp Gly Val Ala Asp Tyr Leu Gln Thr
 1               5                   10                  15

Tyr His Lys Leu Pro Asp Asn Tyr Ile Thr Lys Ser Glu Ala Gln Ala
                20                  25                  30

Leu Gly Trp Val Ala Ser Lys Gly Asn Leu Ala Asp Val Ala Pro Gly
            35                  40                  45

Lys Ser Ile Gly Gly Asp Ile Phe Glu Asn Arg Glu Gly Lys Leu Pro
        50                  55                  60

Gly Lys Ser Gly Arg Thr Trp Arg Glu Ala Asp Ile Asn Tyr Thr Ser
 65                  70                  75                  80

Gly Phe Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110

<210> SEQ ID NO 50
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ala Gln Val Ile Asn Thr Phe Asp Gly Val Ala Asp Tyr Leu Gln Thr
 1               5                   10                  15

Tyr Arg Lys Leu Pro Asp Asn Tyr Ile Thr Lys Ser Glu Ala Gln Ala
                20                  25                  30

Leu Gly Trp Val Ala Ser Lys Gly Asn Leu Ala Asp Val Ala Pro Gly
            35                  40                  45

Lys Ser Ile Gly Gly Asp Ile Phe Ser Asn Arg Lys Gly Glu Leu Pro
        50                  55                  60

Gly Lys Ser Gly Arg Thr Trp Arg Glu Ala Asp Ile Asn Tyr Thr Ser
 65                  70                  75                  80

Gly Phe Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110

<210> SEQ ID NO 51
<211> LENGTH: 110
<212> TYPE: PRT
```

-continued

<213> ORGANISM: Artificial Sequence
<220> FEATURE:
<223> OTHER INFORMATION: Description of Artificial Sequence: Synthetic
      polypeptide

<400> SEQUENCE: 51

Ala Gln Val Ile Asn Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

Lys Ser Ile Gly Gly Asp Ile Phe Ser Asn Arg Glu Gly Lys Leu Pro
    50                  55                  60

Gly Glu Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 52
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ala Gln Val Ile Asn Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

Lys Ser Ile Gly Gly Asp Ile Phe Ser Asn Arg Glu Gly Lys Leu Pro
    50                  55                  60

Gly Lys Asp Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 53
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ala Gln Val Ile Asn Thr Phe Asp Gly Val Ala Asp Tyr Leu Gln Thr
1               5                   10                  15

Tyr Arg Lys Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

```
Lys Ser Ile Gly Gly Asp Ile Phe Ser Asn Arg Glu Gly Lys Leu Pro
 50                  55                  60

Gly Lys Ser Gly Glu Thr Trp Arg Glu Ala Asp Ile Asn Tyr Thr Ser
 65                  70                  75                  80

Gly Phe Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110
```

<210> SEQ ID NO 54
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Ala Gln Val Ile Asn Thr Phe Asp Gly Val Ala Asp Tyr Leu Gln Thr
 1               5                  10                  15

Tyr Arg Lys Leu Pro Asp Asn Tyr Ile Thr Lys Ser Glu Ala Gln Ala
                 20                  25                  30

Leu Gly Trp Val Ala Ser Lys Gly Asn Leu Ala Asp Val Ala Pro Gly
             35                  40                  45

Lys Ser Ile Gly Gly Asp Ile Phe Ser Asn Arg Glu Gly Lys Leu Pro
 50                  55                  60

Gly Lys Ser Gly Arg Thr Trp Arg Glu Ala Asp Ile Ile Tyr Thr Ser
 65                  70                  75                  80

Gly Phe Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110
```

<210> SEQ ID NO 55
<211> LENGTH: 110
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

```
Ala Gln Val Ile Asn Thr Phe Asp Gly Val Ala Asp Tyr Leu Gln Thr
 1               5                  10                  15

Tyr Arg Lys Leu Pro Asp Asn Tyr Ile Thr Lys Ser Glu Ala Gln Ala
                 20                  25                  30

Leu Gly Trp Val Ala Ser Lys Gly Asn Leu Ala Asp Val Ala Pro Gly
             35                  40                  45

Lys Ser Ile Gly Gly Asp Ile Phe Ser Asn Arg Glu Gly Lys Leu Pro
 50                  55                  60

Gly Lys Ser Gly Arg Thr Trp Arg Glu Ala Asp Ile Asn Tyr Asp Ser
 65                  70                  75                  80

Gly Phe Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110
```

<210> SEQ ID NO 56
<211> LENGTH: 110
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 56

Ala Gln Val Ile Asn Thr Phe Asp Gly Val Ala Asp Tyr Leu Gln Thr
1               5                   10                  15

Tyr Arg Lys Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

Lys Ser Ile Gly Gly Asp Ile Phe Ser Asn Arg Glu Gly Lys Leu Pro
    50                  55                  60

Gly Lys Ser Gly Arg Thr Trp Arg Glu Ala Asp Ile Asn Tyr Val Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 57
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Ala Gln Val Ile Asn Thr Phe Asp Gly Val Ala Asp Tyr Leu Gln Thr
1               5                   10                  15

Tyr His Lys Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

Lys Ser Ile Gly Gly Asp Ile Phe Ser Asn Arg Glu Gly Lys Leu Pro
    50                  55                  60

Gly Lys Ser Gly Arg Thr Trp Arg Glu Ala Asp Ile Asn Tyr Thr Glu
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Gln Thr Phe Thr Lys Ile Arg
            100                 105                 110

<210> SEQ ID NO 58
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Ala Gln Val Ile Asn Thr Phe Asp Gly Val Ala Asp Tyr Leu Gln Thr
1               5                   10                  15

Tyr Arg Lys Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

```
Lys Ser Ile Gly Gly Asp Ile Phe Ser Asn Arg Glu Gly Lys Leu Pro
 50                  55                  60

Gly Lys Ser Gly Arg Thr Trp Arg Glu Ala Asp Ile Asn Tyr Thr Ser
 65                  70                  75                  80

Gly Ala Arg Asn Ser Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110

<210> SEQ ID NO 59
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ala Gln Val Ile Asn Thr Phe Asp Gly Val Ala Asp Tyr Leu Gln Thr
 1               5                  10                  15

Tyr Arg Lys Leu Pro Asp Asn Tyr Ile Thr Lys Ser Glu Ala Gln Ala
                20                  25                  30

Leu Gly Trp Val Ala Ser Lys Gly Asn Leu Ala Asp Val Ala Pro Gly
             35                  40                  45

Lys Ser Ile Gly Gly Asp Ile Phe Ser Asn Arg Glu Gly Lys Leu Pro
 50                  55                  60

Gly Lys Ser Gly Arg Thr Trp Arg Glu Ala Asp Ile Asn Tyr Thr Ser
 65                  70                  75                  80

Gly Phe Arg Asn Ala Asp Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110

<210> SEQ ID NO 60
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ala Gln Val Ile Asn Thr Phe Asp Gly Val Ala Asp Tyr Leu Gln Thr
 1               5                  10                  15

Tyr Arg Lys Leu Pro Asp Asn Tyr Ile Thr Lys Ser Glu Ala Gln Ala
                20                  25                  30

Leu Gly Trp Val Ala Ser Lys Gly Asn Leu Ala Asp Val Ala Pro Gly
             35                  40                  45

Lys Ser Ile Gly Gly Asp Ile Phe Ser Asn Arg Glu Gly Lys Leu Pro
 50                  55                  60

Gly Lys Ser Gly Arg Thr Trp Arg Glu Ala Asp Ile Asn Tyr Thr Ser
 65                  70                  75                  80

Gly Phe Arg Asn Ser Lys Arg Ile Leu Tyr Ser Ser Asp Trp Leu Ile
                 85                  90                  95

Tyr Lys Thr Thr Asp His Tyr Gln Thr Phe Thr Lys Ile Arg
                100                 105                 110

<210> SEQ ID NO 61
<211> LENGTH: 110
<212> TYPE: PRT
```

-continued

<213> ORGANISM: Artificial Sequence
<220> FEATURE:
<223> OTHER INFORMATION: Description of Artificial Sequence: Synthetic
      polypeptide

<400> SEQUENCE: 61

```
Ala Gln Val Ile Asn Thr Phe Asp Gly Val Ala Asp Tyr Leu Gln Thr
1               5                   10                  15

Tyr Arg Lys Leu Pro Asp Asn Tyr Ile Thr Lys Ser Glu Ala Gln Ala
            20                  25                  30

Leu Gly Trp Val Ala Ser Lys Gly Asn Leu Ala Asp Val Ala Pro Gly
        35                  40                  45

Lys Ser Ile Gly Gly Asp Ile Phe Ser Asn Arg Glu Gly Lys Leu Pro
    50                  55                  60

Gly Lys Ser Gly Arg Thr Trp Arg Glu Ala Asp Ile Asn Tyr Thr Ser
65                  70                  75                  80

Gly Phe Arg Asn Ser Asp Arg Ile Leu Tyr Ser Ser Asp Trp Leu Ile
                85                  90                  95

Tyr Lys Thr Thr Asp His Tyr Lys Thr Phe Thr Lys Ile Arg
                100                 105                 110
```

(DI)BARNASE-BARSTAR COMPLEXES

This application claims the benefit of the filing date of U.S. Provisional Application Ser. No. 60/539,976 filed Jan. 30, 2004.

SEQUENCE LISTING

The instant application contains a Sequence Listing which has been submitted in ASCII format via EFS-Web and is hereby incorporated by reference in its entirety. Said ASCII copy, created on Dec. 1, 2011, is named SCH2025.txt and is 54,128 bytes in size.

FIELD OF THE INVENTION

The invention relates to multivalent complexes, their production and method of use.

BACKGROUND OF THE INVENTION

Abnormal cellular proliferation, notably hyperproliferation, is the source of numerous diseases, the most severe one being cancer. In the United States alone approximately 1.5 million people are diagnosed with cancer and 0.5 million die from it each year. The fight against cancer has seen some success but also numerous set-backs. There is a great need for innovative therapeutics.

Targeted drug delivery, as opposed to systemic delivery, can dramatically increase drug efficacy while decreasing side effects. Targeted delivery requires a target (antigen, receptor), a delivery vehicle (cytokines, antibodies and fragments thereof) and a drug. Currently, several strategies are used for delivering drugs to targets: they are based either on direct conjugates to the targeting protein or on derivatized carriers that interact with specific adapters that are conjugated to the targeting protein. Recently, heterobifunctional recombinant antibodies recognizing one epitope on the cell surface and another epitope on the drug carrier have been proposed for targeted drug delivery. However, these constructs only make contact with one binding site and therefore show high dissociation rates. The strong interaction of streptavidin with biotin has been particularly widely explored for a targeting approach. Unfortunately, streptavidin is highly immunogenic and furthermore shows an inherent high kidney accumulation.

Over the last few years, a burst of reports on the construction of multivalent recombinant antibody fragments has appeared (Pluckthun, A. and Pack, P. Immunotechnology 3, 83-105, 1997. Todovroska, A. et all., J. Immunol. Methods 248, 47-66, 2001). Multivalency not only enhances the strength of binding, but it also amplifies binding selectivity. These designs have included a variety of recombinant fusions using adhesive protein domains, peptides or specially designed linkers for formation of single chain antibody fragment multimers. For medical applications such as targeting to tumor-associated antigens, efficient tissue penetration must be combined with high functional affinity, and fragments must be stable against denaturation or proteolysis until they have reached the tumor site. Most of these published constructs will not meet all of these prerequisites: multimeric constructs assembled by domains or peptides show dissociation at dilution, multimeric constructs assembled by specific linkers are non-homogeneous products and the production of all of these constructs is hampered by aggregation and subsequent precipitation of the proteins at high protein concentration.

The invention presents a novel method for the design of multimers based on the ribonuclease barnase and its inhibitor, barstar. The complex between barnase and barstar is extremely tight with a $K_d \sim 10^{-14}$ M and forms very rapidly, comparable in affinity with the streptavidin/biotin system (Hnatowich et al., J. Nucl. Med. 28: 1294-1302, 1987).

The barnase and barstar proteins are small (110-residues for barnase and 89-residues for barstar), stable, very soluble and resistant to proteases—features commensurate with bacterial expression. Moreover, the three-dimensional structure of the complex is known both from X-ray crystallography[3] and NMR spectroscopy[4,5] and shows that the N-terminal as well C-terminal parts of both proteins localize outside of the barnase:barstar interface. They are therefore accessible for fusion with targeting proteins and then form extremely stable multimers due to the practically irreversible pairing of these ligands.

In addition barnase and barstar have been used in genetically engineered plants. It has been shown that male fertility can be restored to the plant with a chimeric fertility-restorer gene comprising another DNA sequence (or fertility-restorer DNA) that codes, for example, for a protein that inhibits the activity of the cytotoxic product or otherwise prevents the cytotoxic product to be active in the plant cells (European patent publication "EP" 0,412,911). For example the barnase gene of *Bacillus amyloliquefaciens* codes for an RNase, the barnase, which can be inhibited by a protein, the barstar, that is encoded by the barstar gene of *B. amyloliquefaciens*. The barnase gene can be used for the construction of a sterility gene while the barstar gene can be used for the construction of a fertility-restorer gene. Experiments in different plant species, e.g. oilseed rape, have shown that a chimeric barstar gene can fully restore the male fertility of male sterile lines in which the male sterility was due to the presence of a chimeric barnase gene (EP 0,412,911, Mariani et al., Proceedings of the CCIRC Rapeseed Congress, Jul. 9-11, 1991, Saskatoon, Saskatchewan, Canada; Mariani et al., Nature 357: 384-387, 1992,). By coupling a marker gene, such as a dominant herbicide resistance gene (for example the bar gene coding for phosphinothricin acetyl transferase (PAT) that converts the herbicidal phosphinothricin to a non-toxic compound (De Block et al., EMBO J. 6:2513, 1987), to the chimeric male-sterility and/or fertility-restorer gene, breeding systems can be implemented to select for uniform populations of male sterile plants (EP 0,344,029; EP 0,412,911).

Barnase and barstar have been used in a new approach for effective positive selection during gene manipulation. Several plasmid vectors for molecular cloning were constructed. They are based on the expression plasmid for a bacterial ribonuclease, barnase. In addition to the barnase gene under control of a synthetic tac promoter, these plasmids carry the gene for the barnase inhibitor, barstar, the constitutive expression of which protects the bacterium from the detrimental effects of moderate barnase production. Full expression of the barnase gene overcomes protection by barstar and becomes lethal. The entire pUC polylinker was inserted into the barnase gene for convenient cloning of genes of interest. Uncut or religated vectors will preclude growth while plasmids with inserts in the barnase gene will let the cells survive. The resulting plasmids are generally useful selective cloning vectors representing the <<kill-the-rest>> approach for studies in molecular biology and biotechnology (RU 2105064 C1, 1996).

SUMMARY OF THE INVENTION

The present invention is based on the observation that the ribonuclease barnase and its inhibitor barstar form a very tight complex in which all N and C termini are accessible for fusion.

The invention relates to barnase and barstar used in a modular approach (a) when attached to scFv fragment via a hinge region they serve as building blocks for bivalent miniantibodies.
(b) By fusing more than one barnase (or barstar) in series, complexes of higher valency can be created.
(c) By fusing different scFv fragments to barnase and barstar, homo- as well as heteromultimeric proteins complexes can be designed.

The invention relates to heteromultimeric proteins carrying antibody fragments or peptide homing fragments and fused to the second partner carrying any type of diagnostic or therapeutic protein or peptide or vice versa.

In particular the invention relates to barnase: barstar complexes of exact stoichiometric ratio of partners.

The invention further relates to production of barnase fusions by barstar coexpression and a method of removing barstar fixed on solid support.

The invention also relates to the use of a barnase and barstar derivative according to the invention in a method of diagnosis of a neoplastic disease or in a method of treatment of a mammal suffering from a neoplastic disease.

The invention also relates to the use of barnase and barstar derivatives as a method of visualization, said visualization units being directly bonded together through chemical groups or backbone moieties of adjacent said visualization units, or linked by a coupling agent covalently bonded to chemical groups or backbone moieties of adjacent said visualization units.

Said visualization unit being an enzyme, wherein the enzymatic site is the visualization site, a tagged natural or synthetic polypeptide, a tagged polyol, a tagged polyolefin or a tagged polycarbohydrate wherein the tag of the tagged polypeptide, tagged polyol, tagged polyolefin or tagged polycarbohydrate is the visualization site thereof; and the tag of said tagged polypeptide, tagged polyol, tagged polyolefin or tagged carbohydrate is a fluorescent group, a dye, a radioactive group, a photon emitter or an electron dense group.

Said visualization unit is combinatorially labeled with a fluorophore selected from the group consisting of the fluorophores FITC, Cy3, Cy3.5, Cy5, Cy5.5 and Cy7.

Said visualization unit being a radioactive isotope. Radioactive isotopes considered are radiometalls such as $^{94m}$Tc, $^{99m}$Tc, $^{188}$Re, $^{186}$Re, $^{111}$In, $^{90}$Y, $^{64}$Cu, $^{67}$Cu and Lu, in particular $^{99m}$Tc, $^{88}$Re, $^{186}$Re and $^{111}$In.

The invention further relates to pharmaceutical compositions comprising barnase and barstar derivatives of the invention, in particular pharmaceutical compositions suitable for diagnostic applications and pharmaceutical compositions suitable for therapeutic applications, and to the use of such pharmaceutical compositions in a method of diagnosis and in a method of therapeutic treatment, respectively.

The invention also relates to intermediates for the preparation of compounds useful in a diagnostic or therapeutic treatment according the invention, in particular to compounds substituted with radioactive isotopes. Radioactive metals considered are radioisotopes such as $^{94m}$Tc, $^{99m}$Tc, $^{188}$Re, $^{186}$Re, $^{111}$In, $^{90}$Y, $^{64}$Cu, $^{67}$Cu and $^{177}$Lu, in particular $^{99m}$Tc, $^{188}$Re, $^{18}$Re and $^{111}$In.

DETAILED DESCRIPTION OF THE INVENTION

Figure 1:
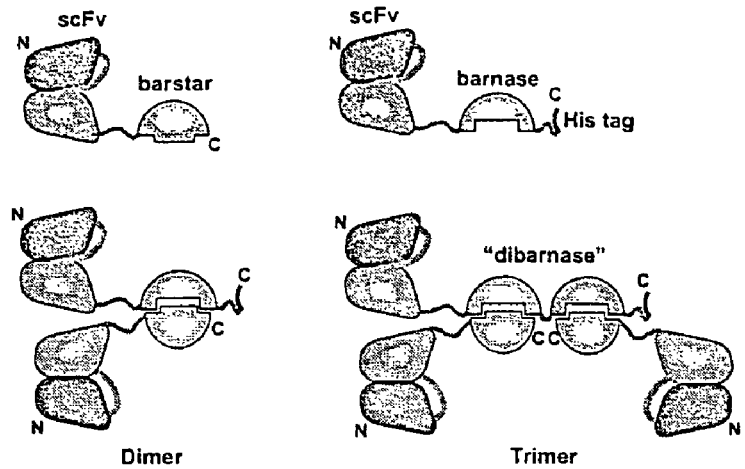
FIG. 1. The concept of creating multimeric miniantibodies using heterodimeric barnase:barstar module and scFv fragments. Engineering of scFv fusion proteins with barstar and barnase or dibarnase yields dimeric and trimeric complexes due to ligand pairings.
Figure 2:
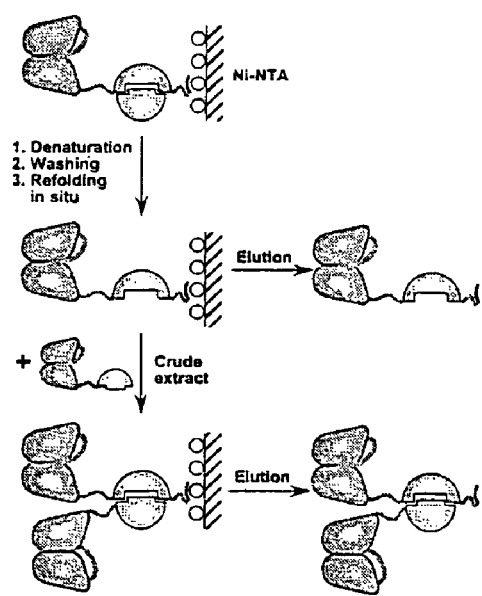
FIG. 2. Schematic representation of homogeneous preparation of mono- and multivalent proteins. Expression of scFv-barnase fusion proteins requires co-expression of the barnase inhibitor, barstar; denaturation of the His-tag-immobilized scFv-barnase:barstar complex removes the inhibitor and, following refolding of the Ni$^{2+}$-NTA adsorbed fusion protein, results in its functional preparation. The affinity chromatography based on the His-tag-immobilized scFv-barnase fusions and saturation of the column with scFv-barstar protein (without His-tag) results in one-step preparation of oligomeric complexes with an exact stoichiometric ratio of subunits.
Figure 3:
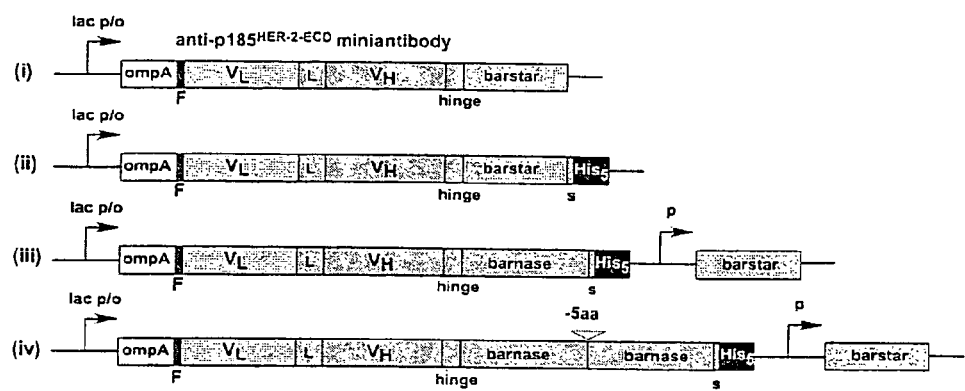
FIG. 3. Overview of the gene constructs for expression of the 4D5 scFv-barstar (I), 4D5 scFv-barstar-His$_5$ (II) (His$_5$ tag disclosed as SEQ ID NO: 10), 4D5 scFv-barnase-His$_5$ (III) (His$_5$ tag disclosed as SEQ ID NO: 10) and 4D5 scFv-dibarnase-His$_5$ (IV) (His$_5$ tag disclosed as SEQ ID NO: 10) fusion proteins. The triangle in construct IV indicates a deletion of the five N-terminal amino acids of the second barnase. Inducible expression of the gene fusions is under transcriptional control of the lac promoter and the ompA signal peptide is used to direct secretion of the recombinant proteins produced to the periplasmic space of E. coli. Barstar coexpression under the control of constitutive promoter (p) is required to suppress cytotoxicity of barnase fusions FIG. 4. 12% SDS-PAGE documenting the purification of monovalent fusion proteins and multimeric complexes. (I) Coomassie stained gel; (II, III) Western blot analysis screened with anti-barstar and anti-barnase sera, respectively. The same blot was used for both Western probing after stripping the first detecting antiserum. Lanes are: 1-4D5 scFv fragment, 2-4D5 scFv-barstar-His$_5$ (His$_5$ to disclosed as SEQ ID NO: 10), 3-4D5 scFv-barnase-His$_5$ (His$_5$ tag disclosed as SEQ ID NO: 10), 4-4D5 scFv-dibarnase-His$_5$ (His$_5$ tag disclosed as SEQ ID NO: 10), 5-dimeric complex, 6-trimeric complex, 7-markers FIG. 5. Assembly of multimeric proteins and their antigen binding. Association of 4D5 scFv-barnase-His$_5$ (his$_5$ tag disclosed as SEQ ID NO: 10) and 4D5-scFv-dibarnase-His$_5$ (His$_5$ to disclosed as SEQ ID NO: 10) with their partner 4D5 scFv-barstar fusion. The preparations were separated on a gel filtration column. In this assay the elution peak of nonlabeled 4D5 scFv-barstar (solid line) was shifted from an apparent molecular weight of 39.9 kDa to 81 kDa when associated with radiolabeled 4D5 scFv-dibarnase-His$_5$ (dotted line) (His$_5$ tag disclosed as SEQ ID NO: 10).
Figure 4:
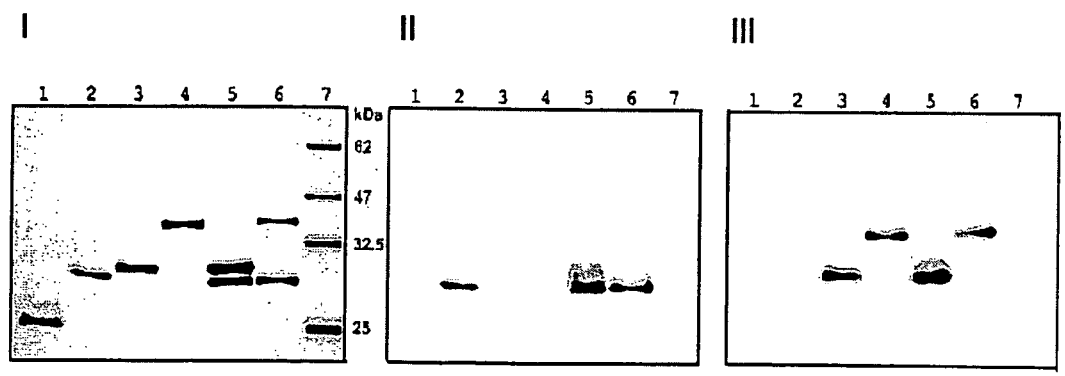
Figure 5:
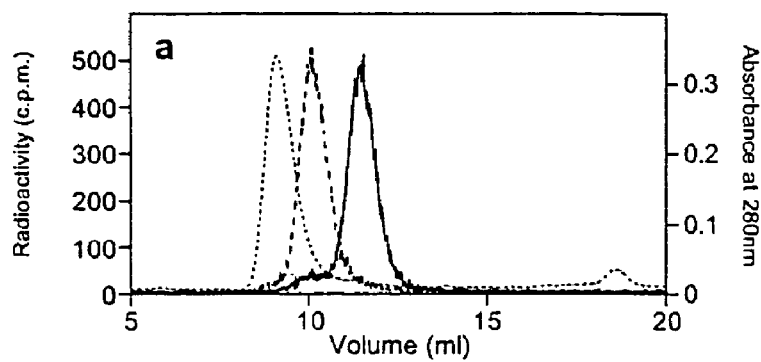
Figure 6:
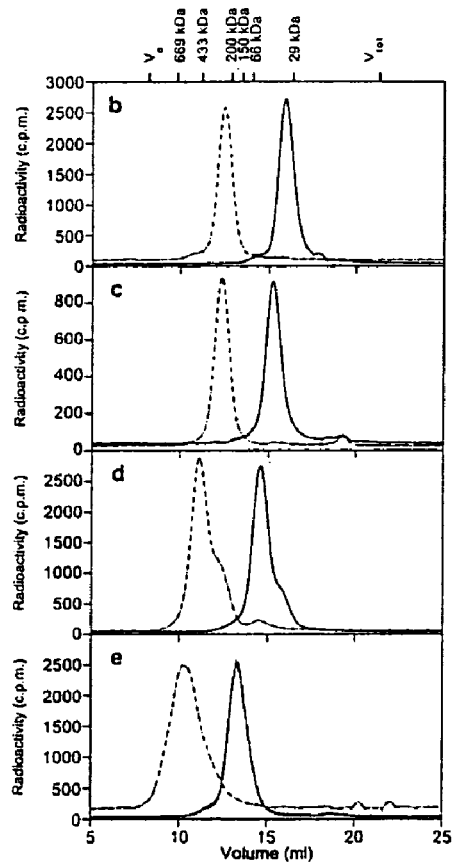
FIG. 6. Antigen binding of radiolabeled mono-, di- and trimeric 4D5 scFv-barnase-barstar constructs. The shift in molecular weight was followed on a gelfiltration column when the antibodies were mixed with soluble recombinant p185-HER2-ECD antigen. Gelfiltration analysis of the derivative mixed with TCl (shift of the peak from 1.5 kDa to 70 kDa)
Figure 7:
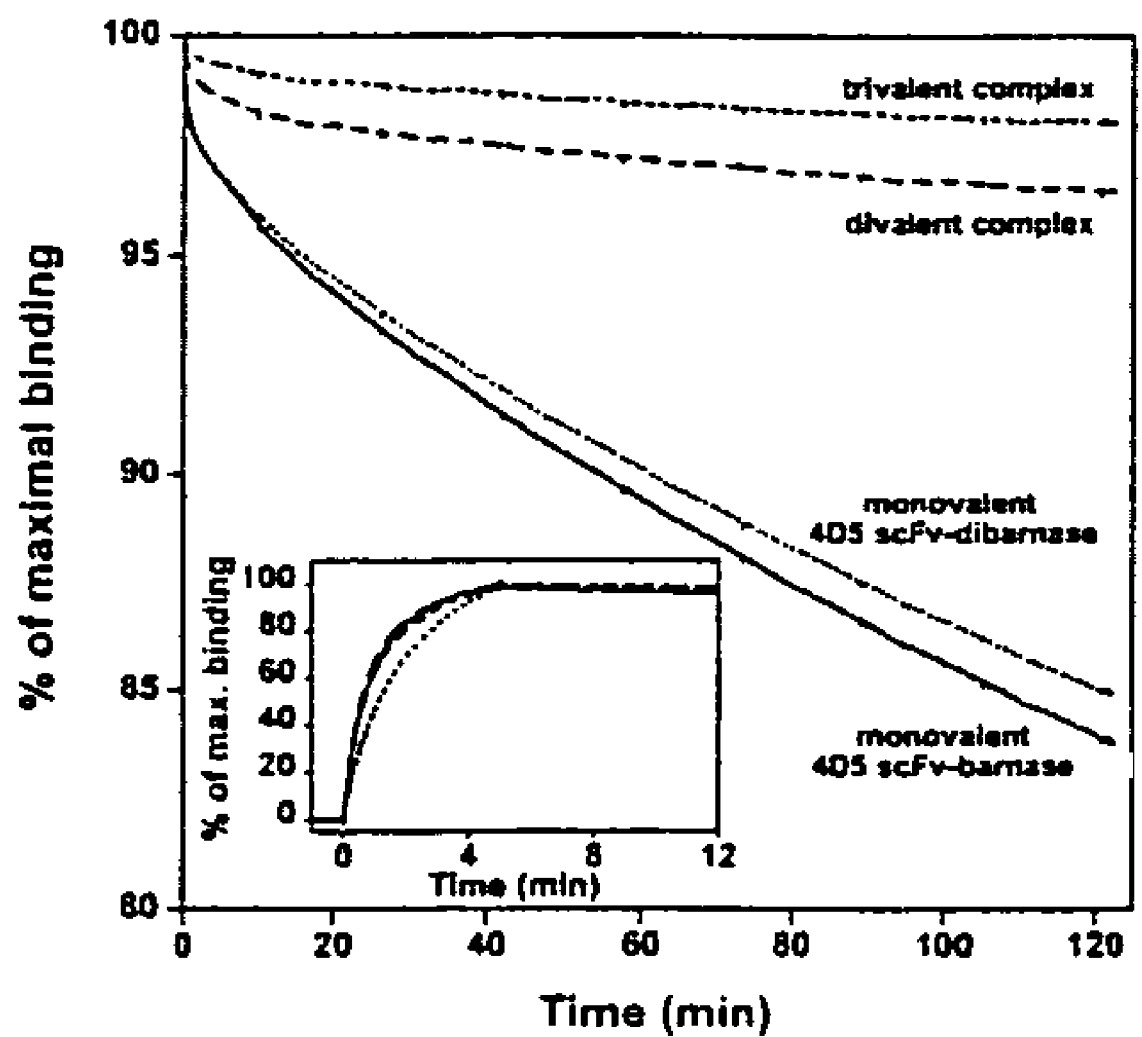
FIG. 7. Dissociation kinetics of monomeric, dimeric and trimeric 4D5 scFv-constructs measured by surface plasmon resonance.

A barnase as used herein is any protein which is capable of degrading single-stranded RNA and which comprises the amino acid sequence of barnase (secreted barnase) as secreted by *Bacillus amyloliquefaciens* (SEQ ID NO: 11) (Hartley, 1988, J. Mol. Biol. 202:913) or an amino acid sequence having at least 80%, preferably at least 85% sequence identity with this sequence. Barnases, as used herein are capable of degrading RNA by a reaction which involves the initial cleaving of the phosphodiester bond between the 5' ribose of one nucleotide and the phosphate group attached to the neighbouring 3' nucleotide. The initial product of this reaction is a 2',3'-cyclic phosphate intermediate which is subsequently hydrolyzed to the corresponding 3' nucleoside phosphate. Barnases are also capable of hydrolyzing polyethenoadenosine phosphate to yield a highly fluorogenic nucleotide analogue 1,N-ethenoadenosine (Fitzgerald and Hartley, Anal. Biochem. 214:544-547, 1993,) and have at least 10% of the activity of secreted barnase as measured under standard conditions (Fitzgerald and Hartley, Anal. Biochem. 214:544-547, 1993; Hartley, Biochemistry 32:5978-5984, 1993,). Barnases are further capable of specific binding to wild-type barstar (see below) with a dissociation constant of $10^{-12}$ M or less, preferably with a dissociation constant of the order $10^{-13}$ M to $10^{-14}$M (Schreiber and Fersht, Biochemistry 32:5145-5150, 1993; Hartley, Biochemistry 32:5978-5984, 1993).

Binase is the extracellular ribonuclease secreted by *Bacillus intermedius* (Schulga et al, NAR 20:2375, 1992) and is also considered to be a barnase as used in this invention.

For convenience barnase, as used in the description or in the Examples below, will designate a protein having the amino acid sequence of the barnase encoded by pVE108 (SEQ ID NO: 36) (WO 92/09696).

A barstar is any protein that is capable of specific binding to secreted barnase with a dissociation constant of $10^{-12}$ M or less, preferably with a dissociation constant of the order of $10^{-13}$ M to $10^{-14}$ M (Schreiber and Fersht, Biochemistry 32:5145-5150, 1993; Hartley, Biochemistry 32:5978-5984, 1993). Barstars are capable of inhibiting at least 50%, particularly at least 75%, more particularly at least 90% of the activity of secreted barnase in an equimolar mixture of barstar and secreted barnase in standard conditions (Hartley, Biochemistry 32:5978-5984, 1993). A barstar is a protein comprising the amino acid sequence of (SEQ ID NO: 12) (Hartley, J. Mol. Biol. 202:913, 1988) or an amino acid sequence having at least 80%, preferably at least 85% sequence identity with this sequence. Wild type barstar is the barstar produced by *Bacillus amyloliquefaciens* and having the amino acid sequence of (SEQ ID NO: 12) (Hartley, J. Mol. Biol. 202:913, 1988). It goes without saying that barstars as used herein include for example the biologically active barstar mutants described by Hartley (SEQ ID NOs: 13-35) (Hartley, Biochemistry 32:5978-5984, 1993).

A barnase DNA (or barnase coding sequence) as used herein is any DNA fragment having a nucleotide sequence coding for a barnase. A particularly preferred barnase DNA is the barnase DNA as present in pVE108 (SEQ ID NO: 36) (WO 92/09696).

A barstar DNA (or barstar coding sequence) as used herein is any DNA fragment having a nucleotide sequence coding for a barstar. A wild type barstar DNA is the DNA which codes for wild-type barstar (SEQ ID NO: 12) and which has the nucleotide sequence as described (Hartley, J. Mol. Biol. 202:913, 1988).

Compounds of fusions of barnase to antibody scFv fragments or antibody VL domains (Martsey, S. P., et all., Protein Eng. 17, 85-93, 2004), but not restricted to these examples.

Compounds of fusion of barstar to antibody scFv fragments, but not restricted to these examples.

Compounds of formula mentioned useful in a method of diagnostic and/or therapeutic treatment according to the invention.

Radioactive metals considered are radioisotopes such as $^{94m}$Tc, $^{99m}$Tc, $^{188}$Re, $^{186}$Re, $^{111}$In, $^{90}$Y, $^{64}$Cu, $^{67}$Cu and $^{177}$Lu, in particular $^{99m}$Tc, $^{188}$Re, $^{186}$Re and $^{111}$In.

Compounds of the invention carrying an antiproliferative agent are useful for transporting the agent in an inactive form in to the hyperproliferative cells where it can exert its action after intracellular amidolysis.

In a method of treatment of a neoplastic and/or infectious disease, a compound of the invention carrying a suitable therapeutic agent can be administered alone or in combination with one or more other therapeutic agents, possible combination therapy taking the form of fixed combinations, or the administration of a compound of the invention and one or more other therapeutic agents being staggered or given independently of one another, or the combined administration of fixed combinations and one or more other therapeutic agents. A compound of the invention can, besides or in addition, be administered especially for tumor therapy in combination with chemotherapy, immunotherapy, surgical intervention, or a combination of these. Long-term therapy is equally possible as is adjuvant therapy in the context of other treatment strategies.

The invention further relates to pharmaceutical compositions comprising barnase/barstar derivatives of the invention, in particular pharmaceutical compositions suitable for diagnostic applications and pharmaceutical compositions suitable for therapeutic applications.

Preferred are pharmaceutical compositions for parenteral administration, such as intravenous, intramuscular or subcutaneous administration. The compositions comprise the active ingredient alone or together with a pharmaceutically acceptable carrier. The dosage of the active ingredient depends upon the disease to be treated and upon the species, its age, weight, and individual condition, the individual pharmacokinetic data, and the mode of administration.

METHODS OF MANUFACTURE

Compounds of the invention are prepared by standard methods known in the art. The following Examples serve to illustrate the invention without limiting the invention in its scope.

EXAMPLES

Reagent grade chemicals were from Sigma or Fluka, Buchs (CH) and were used without further purification. Rabbit anti-barnase and rabbit anti-barstar sera was provided by R. W. Hartley, Bethesda, NIH, USA FPLC analyses were performed on a BioLogic DuoFlow system equipped with a EG&G Berthold LB 508 radiometric detector, using Superdex 75 and Superdex 200 columns at a flow rate of 1 ml/min. Chromatograms were recorded at 280 nm. Solvent were predominantly aqueous buffers.

Example 1

Construction of Expression Plasmids

The plasmids for the periplasmic expression of scFv-barnase and barstar fusion proteins are based on the vector pIG64D5 (Knappik, A. & Plückthun, A. Protein Eng. 8, 81-89, 1995).

The barstar and barnase genes were amplified out of the plasmid pMT413 (Hartley, R. W. Biochemistry 32,5978-5984, 1993) using the primers AscI_bs-fwd: 5'-TG-GCGCGCCGAAAAAAGCAGTCATTAACGGG-3' (SEQ ID NO: 1), bs_AscI-rev: 5'-CG GCGCGCCAGAAAGTAT-GATGGTGATGTC-3' (SEQ ID NO: 2), AscI_bn-fwd:

5'-GTGGCGCGCCTGCACAGGTTATCAACACGTTTG-3' (SEQ ID NO: 3) and bn_AscI-rev: 5'-GTGCGGCGCGC-CTCTGATTTTTGTAAAGGTCTG-3'(SEQ ID NO: 4). The AscI fragments were ligated into the vector pIG64D5. The plasmid encoded fusion protein: VL-linker-VH-hinge-barstar-His$_5$-tag (His$_5$ tag disclosed as SEQ ID NO: 10) was easily obtained. In contrast, no clones with the correct barnase gene were found. To obtain 4D5 scFv-barstar derivative without a His-tag, the BspEI/HindIII fragment was cut out from the 4D5 scFv-barstar-His$_5$ (His$_5$ tag disclosed as SEQ ID NO: 10) encoding plasmid and replaced by BspEI/HindIII part from the plasmid pMT413. To introduce the barstar gene for bicistronic transcription followed by the scFv-barnase encoding gene barstar gene was amplified out of the plasmid pMT413 using primers HindIII_bs-fwd: 5'-CGTCTAAGCT-TGATGAAAAAAGCAGTCATTAACG-3' fSEQ ID NO: 5) and bs_HindIII-rev: 5'-AACAGCTATGACCATGATTACG-3' (SEQ ID NO: 6) and ligated into the HindIII-digested plasmid pIG64D5. The resulting plasmid was used for cloning of barnase gene flanked by AscI sites. To introduce in pIG64D5 vector the barstar gene under a control of its own promotor the fragment was amplified out of the plasmid pMT413 using primers HindIII_pbs-fwd: 5'-ATCAGAC-CTTTACAAAAAGCTTATAAC-3' (SEQ ID NO: 7) and bs_HindIII-rev and cloned via HindIII site. The obtained vector was used to attach barnase gene to 4D5scFv fragment using AscI site. The resulting plasmid had no mutations and encoded the fusion protein: VL-linker-VH-hinge-barnase-His$_5$-tag (His$_5$ tag disclosed as SEQ ID NO: 10). The plasmid carrying the dimeric barnase fragment instead of barnase was derived analogously using overlap extension PCR and primers dibn-fwd: 5'-CAGACCTTTACAAAAATCAGAGA-CACGTTTGACGGGGTTGC-3' (SEQ ID NO: 8), dibn-rev: 5'-GCAACCCCGTCAAACGTGTCTCT-GATTTTTGTAAAGGTCTG-3' (SEQ ID NO: 9), AscI_bn-fwd and bn_AscI-rev.

Example 2

Molecular Modeling

The models are based-on the X-ray structures of humanized anti-p185$^{HER2-ECD}$ antibody 4D5 version 8 (PDB entry 1FVC, 2.2 Å resolution)[14] and the structure of the barnase: barstar complex (PDB entry 1BGS, 2.6 A resolution)[15]. The flexible tags, linkers and hinge residues were modeled as beta strands and shaped by simulated melting and annealing using the Discover module of the InsightII molecular modeling suite (MSI/Biosym, San Diego).

Example 3

Freshly transformed *E. coli* K12 strain SB536 (Bass, S. et al., J. Bacteriol. 178, 1154-61, 1996) (F-, WG1, ΔfhuA (ton Δ), ΔhhoAB (SacII), shh) cells, grown in SB medium containing 0.1 g/L ampicillin; lac promoter was induced with 1 mM IPTG at an OD550=0.7. Expression was allowed to continue for 16 h at 27° C. Cells were harvested by centrifugation at 6000 rpm for 15 min at 4° C. Cell extracts were prepared by French press lysis at 10,000 psi and centrifugation at 20,000 rpm for 1 h. The supernatants were applied to a Ni2+-NTA column (Qiagen, Germany) according to the manufacturer's instructions. The immobilized proteins were denaturated with 6 M GuHCl in PBS, pH 8.0, refolded using linear gradient 6-0 M GuHCl in the same buffer, washed with 25 mM imidazole and eluted with 200 mM imidazole. For final purification of 4D5 scFv-barnase-His$_5$ (His$_5$ tag disclosed as SEQ ID NO: 10) and 4D5 scFv-dibarnase-His$_5$ (His$_5$ tag disclosed as SEQ ID NO: 10) elution fractions were directly applied onto a Protein-A Sepharose column (Pharmacia) and eluted with 0.1 M sodium citrate, pH 3.5; the eluate was immediately neutralized with 1 M Tris. For preparation of dimeric and trimeric complexes 4D5 scFv-barnase-His$_5$ (His$_5$ tag disclosed as SEQ ID NO: 10) or 4D5 scFv-dibarnase-His$_5$ (His$_5$ tag to disclosed as SEQ ID NO: 10), respectively, were immobilized onto Ni2+-NTA column and saturated with diluted 1:100 with PBS cleared cell lysate containing 4D5 scFv-barstar. Alternatively, the isoluble periplasmic protein was solubilized with 6 M GuHCl in PBS, pH 8, centrifugated 20.000 rpm for 30 minutes and diluted 1:200 with PBS, pH 8. After extensive washing with 25 mM imidazole, 1 M NaCl in PBS the resulting complexes were eluted with 200 mM imidazole, 300 mM NaCl in PBS and dialyzed against 300 mM NaCl, 10% glycerol in PBS. MW (MS, MALDI data) 4D5 scFv-barstar, 38830 (39109 theor.), 4D5 scFv-barstar-His$_5$ (His$_5$ tag disclosed as SEQ ID NO: 10) 39880 (39885 theor.), 4D5 scFv-barnase-His$_5$ (His$_5$ tag disclosed as SEQ ID NO: 10), 42110 (42120 theor.), and 4D5 scFv-dibarnase-His$_5$ (His$_5$ tag disclosed as SEQ ID NO: 10), 54060 (54074 theor.).

Example 4

Surface Plasmon Resonance Biosensor

Measurements were performed with a BIAcore instrument (BIACORE 3000, Sweden). Recombinant p185$^{HER2-EcD}$ was coupled onto a CM5 chip at a density of 4500 RU by standard amine coupling chemistry. All proteins were used at the same concentration, 1.60 nM in PBS, pH7.4, with 0.005% of Tween-20. The sensograms were obtained at a flow rate of 30 µl/min at 15° C. and the dissociation phase was followed for 120 min.

Example 5

SDS-PAGE and Western Blot Analysis

SDS-PAGE analyses were performed under reducing conditions according to standard protocols using 12 and 18% polyacrylamide gels. Immunoblots on Immobilon-P transfer membrane (Millipore, USA) were carried out according to the manufacturers instructions using rabbit anti-barstar serum followed by a goat anti-rabbit IgG peroxidase conjugate (Sigma, USA) for detection. The blots were visualized with chemiluminescent Pierce Supersignal ECL reagent (Pierce, USA). The same membrane was reprobed after stripping for immunodetection with the rabbit anti-barnase serum. Stripping was performed in 100 mM 2-mercaptoethanol, 2% SDS, 65 mM Tris-HCl, pH 7.0 at 60° C. for 1 h.

Example 6

$^{99m}$Tc Radiolabeling Conditions and Stability Studies

All constructs were concentrated to 5 to 10 µM by centrifugation with a 10 kDa cutoff membrane (Ultrafree-MC, Millipore, Bedford, Mass.). Constructs were mixed 1:1 with freshly synthesized $^{99m}$Tc-tricarbonyl trihydrate, as described (Waibel, R. et al., Nat. Biotechnol 17, 897-901, 1999). Labeling efficiency was >95%. Labeled constructs were incubated with human sera 1:10 at 37° C. and analyzed on a gel filtration column (Superdex200), connected to a UV-monitor and a HPLC radioactivity monitor (LB 508, Berthold, Bad Wildbach, Germany). The elution profiles were compared to those of the initial constructs.

Example 7

Immunoreactivity

For immunoreactivity studies, recombinant p185$^{HER2-ECD}$ antigen (10 μg) was mixed with 5×10$^4$ Bq (30 ng) of labeled construct for 30 min at room temperature and separated on a Superdex200 gel filtration column.

Example 8

Bioreactivity

The bioreactivity was defined as the counts of fraction eluting with the higher molecular weight peaks (analytical gel-shift assay).

Example 9

Blood Clearance

Blood clearance studies were performed in xenografted nu/nu mice. They were injected with 10 μg (22 MBq) of 99mTc-labeled constructs in 100 μl PBS. Blood samples were taken at 7.5, 15, 30, 60, 120, and 240 min after injection.

Example 10

Organ Distribution

For organ distribution, animals were sacrificed at 24 h and 48 h after injection and tissues were collected and measured in a gamma counter. For the tumor targeting study, groups of 3 mice each were xenografted with 10$^7$ SK-OV-3 cells (#HTB77, ATCC, Rockville, Md.) on the left side and with 10$^7$ SK-BR-3 cells (3HTB30, ATCC) on the right side and were injected with the radiolabeled constructs two weeks later, when the tumors have reached a size of about 40 mg.

TABLE 1

Biodistribution of $^{99m}$Tc-labeled mono-, di- and trimeric 4D5-barnase-barstar constructs in nu/nu mice after 24 h
Percentage of injected dose per gram of organ

| Organ | monomeric 24 h | dimeric 24 h | trimeric 24 h |
|---|---|---|---|
| Blood | 0.09 ± 0.01 | 0.57 ± 0.17 | 0.88 ± 0.15 |
| Heart | 0.20 ± 0.07 | 1.84 ± 0.34 | 2.47 ± 0.62 |
| Lung | 0.31 ± 0.07 | 1.25 ± 0.28 | 2.54 ± 0.30 |
| Spleen | 0.24 ± 0.21 | 2.90 ± 0.58 | 4.91 ± 1.14 |
| Kidney | 140.63 ± 2.83 | 56.43 ± 7.64 | 21.16 ± 0.72 |
| Stomach | 0.31 ± 0.11 | 0.80 ± 0.17 | 0.91 ± 0.26 |
| Intestine | 0.31 ± 0.01 | 1.15 ± 0.03 | 1.73 ± 0.38 |
| Liver | 1.61 ± 0.21 | 4.56 ± 0.42 | 14.29 ± 0.51 |
| Muscle | 0.18 ± 0.05 | 0.57 ± 0.09 | 0.72 ± 0.15 |
| Bone | 0.16 ± 0.11 | 0.67 ± 0.49 | 1.71 ± 0.59 |
| SKOV3 | 0.97 ± 0.32 | 3.43 ± 1.01 | 7.04 ± 2.35 |
| SKBR3 | 1.91 ± 0.79 | 5.91 ± 2.30 | 9.80 ± 0.82 |
| T/B SKOV3 | 10.80 ± 4.70 | 6.01 ± 3.56 | 8.00 ± 4.03 |
| T/B SKBR3 | 21.20 ± 11.05 | 10.37 ± 7.12 | 11.10 ± 2.83 |

TABLE 2

Biodistribution of $^{99m}$Tc-labeled mono-, di- and trimeric 4D5-barnase-barstar constructs in nu/nu mice after 48 h

| Organ | monomeric 48 h | dimeric 48 h | trimeric 48 h |
|---|---|---|---|
| Blood | 0.05 ± 0.01 | 0.20 ± 0.04 | 0.30 ± 0.04 |
| Heart | 0.14 ± 0.01 | 1.16 ± 0.25 | 1.39 ± 0.24 |
| Lung | 0.17 ± 0.01 | 0.81 ± 0.03 | 1.19 ± 0.12 |
| Spleen | 0.46 ± 0.07 | 3.64 ± 1.72 | 5.00 ± 1.28 |
| Kidney | 106.00 ± 6.04 | 40.49 ± 6.47 | 15.95 ± 0.98 |
| Stomach | 0.18 ± 0.05 | 0.48 ± 0.15 | 0.33 ± 0.13 |
| Intestine | 0.15 ± 0.01 | 0.97 ± 0.25 | 1.00 ± 0.10 |
| Liver | 1.04 ± 0.06 | 3.44 ± 0.43 | 12.92 ± 2.80 |
| Muscle | 0.08 ± 0.01 | 0.26 ± 0.07 | 0.46 ± 0.11 |
| Bone | 0.12 ± 0.10 | 0.54 ± 0.58 | 1.06 ± 0.18 |
| SKOV3 | 0.47 ± 0.16 | 3.34 ± 0.44 | 4.56 ± 1.00 |
| SKBR3 | 0.65 ± 0.20 | 5.38 ± 1.39 | 8.11 ± 0.41 |
| T/B SKOV3 | 9.41 ± 5.08 | 16.70 ± 5.54 | 15.20 ± 5.32 |
| T/B SKBR3 | 13.00 ± 6.60 | 26.9 ± 12.33 | 27.03 ± 4.96 |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure of all applications, patents and publications, cited herein and of corresponding U.S. Provisional Application Ser. No. 60/539,976, filed Jan. 30, 2004, is incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A complex comprising a *Bacillus amyloliquefaciens* barnase bound with high affinity to a *Bacillus amyloliquefaciens* barstar, and further comprising a cobalamin compound which is bound to an N-terminal end or a C-terminal end of said *Bacillus amyloliquefaciens* barnase or said *Bacillus amyloliquefaciens* barstar, wherein
   said *Bacillus amyloliquefaciens* barnase is
   (a) a polypeptide which comprises the amino acid sequence set forth in SEQ ID NO: 11; or
   (b) a polypeptide which comprises at least 98% sequence identity to the amino acid sequence set forth in SEQ ID NO: 11; and
   said *Bacillus amyloliquefaciens* barstar is
   (a) a polypeptide which comprises the amino acid sequence set forth in SEQ ID NO: 12; or
   (b) a polypeptide which comprises at least 98% sequence identity to the amino acid sequence set forth in SEQ ID NO: 12.

2. A complex comprising a *Bacillus amyloliquefaciens* dibarnase bound with high affinity to *Bacillus amyloliquefaciens* barstar, and further comprising cobalamin compound which is bound to an N-terminal end or a C-terminal end of said *Bacillus amyloliquefaciens* dibarnase or said *Bacillus amyloliquefaciens* barstar, wherein
   said *Bacillus amyloliquefaciens* dibarnase comprises two units of *Bacillus amyloliquefaciens* barnase, each of which is, independently
   (a) a polypeptide which comprises the amino acid sequence set forth in SEQ ID NO: 11; or
   (b) a polypeptide which comprises at least 98% sequence identity to the amino acid sequence set forth in SEQ ID NO: 11; and
   said *Bacillus amyloliquefaciens* barstar is
   (a) a polypeptide which comprises the amino acid sequence set forth in SEQ ID NO: 12; or
   (b) a polypeptide which comprises at least 98% sequence identity to the amino acid sequence set forth in SEQ ID NO: 12.

3. A pharmaceutical composition comprising the complex of claim 1 and a pharmaceutically acceptable carrier.

4. The complex according to claim 1, wherein the polypeptide which comprises at least 98% sequence identity to the amino acid sequence set forth in SEQ ID NO: 12 is a polypeptide which comprises the amino acid sequence set forth in SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 28, SEQ ID NO: 29, SEQ ID NO: 30, SEQ ID NO: 31, SEQ ID NO: 32, SEQ ID NO: 33, SEQ ID NO: 34 or SEQ ID NO: 35.

5. The complex according to claim 1, wherein the polypeptide which comprises at least 98% sequence identity to the amino acid sequence set forth in SEQ ID NO: 11 is a polypeptide which comprises the amino acid sequence set forth in SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60 or SEQ ID NO: 61.

6. The complex according to claim 2, wherein the polypeptide which comprises at least 98% sequence identity to the amino acid sequence set forth in SEQ ID NO: 12 is a polypeptide which comprises the amino acid sequence set forth in SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 28, SEQ ID NO: 29, SEQ ID NO: 30, SEQ ID NO: 31, SEQ ID NO: 32, SEQ ID NO: 33, SEQ ID NO: 34 or SEQ ID NO: 35.

7. The complex according to claim 2, wherein the polypeptide which comprises at least 98% sequence identity to the amino acid sequence set forth in SEQ ID NO: 11 is a polypeptide which comprises the amino acid sequence set forth in SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60 or SEQ ID NO: 61.

8. A pharmaceutical composition comprising the complex of claim 2 and a pharmaceutically acceptable carrier.

* * * * *